US00PP28643P3

(12) United States Plant Patent
Meyer

(10) Patent No.: US PP28,643 P3
(45) Date of Patent: Nov. 14, 2017

(54) ***HEMEROCALLIS* PLANT NAMED 'ORANGE SMOOTHIE'**

(50) Latin Name: ***Hemerocallis* (L.) hybrid**
Varietal Denomination: Orange Smoothie

(71) Applicant: Chris Meyer, Zeeland, MI (US)

(72) Inventor: Chris Meyer, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 74 days.

(21) Appl. No.: 14/999,033

(22) Filed: Mar. 22, 2016

(65) Prior Publication Data

US 2017/0280606 P1 Sep. 28, 2017

(51) Int. Cl.
*A01H 5/02* (2006.01)

(52) U.S. Cl.
USPC ..... Plt./312

(58) Field of Classification Search
USPC ..... Plt./312
See application file for complete search history.

*Primary Examiner* — Anne Grunberg

(57) ABSTRACT

A new and distinct *Hemerocallis* plant named 'Orange Smoothie' characterized by winter-hardy compact habit with clean medium-green foliage that goes dormant in the winter; rounded, fragrant, single flowers of orange-mango-colored base with light rose eye, pink midrib and light green throat; tepals with consistent and considerable wavy margins and recurved at apex giving more color from flower backside; scapes of up to 60 cm tall with four-way branching and 32 flowers beginning about mid-July and with repeating scapes through summer for about seven weeks.

1 Drawing Sheet

Botanical classification: *Hemerocallis* (L.) hybrid.
Variety denomination: 'Orange Smoothie'.

BACKGROUND AND ORIGIN OF THE PLANT

The present invention relates to a new and distinct daylily plant, *Hemerocallis* 'Orange Smoothie' hereinafter also referred to as the new plant or just the cultivar name, 'Orange Smoothie'. *Hemerocallis* 'Orange Smoothie' was hybridized by the inventor, Chris Meyer, in the spring of 2000 in a greenhouse at a wholesale perennial nursery in Zeeland, Mich., USA. The new plant originated from a breeding program conducted by the inventor with the specific intention to improve the garden worthiness, expand color regimens and increase flowering period which were some of the criteria of further trials in the trial beds at the same nursery in Zeeland, Mich. The female or seed parent was the proprietary unreleased hybrid *Hemerocallis* 95-104-2 (not patented) and the male or pollen parent was the proprietary unreleased hybrid *Hemerocallis* 96-20-5 (not patented). The new plant was selected as a single seedling from this cross and after confidential evaluations in a trial bed beginning in 2002 in Zeeland, Mich. was assigned the breeder code 00-40-6. The new plant has been asexually propagated by division at the same wholesale nursery in Zeeland, Mich. since 2003 with all resultant asexually propagated plants having retained all the same unique traits as the original plant. *Hemerocallis* 'Orange Smoothie' is stable and reproduces true to type in successive generations of asexual reproduction.

No plants of *Hemerocallis* 'Orange Smoothie' have been sold, in this country or anywhere in the world, prior to the filing of this application, nor has any disclosure of the new plant been made prior to the filing of this application with the exception of that which was disclosed within one year of the filing of this application and was either derived directly or indirectly from the inventor.

There are over 82,000 registered daylilies with The American *Hemerocallis* Society, which is the International Cultivar Registration Authority for the genus *Hemerocallis*. In comparison to the female parent 95-104-2, the new plant has a mango orange flower color and the female parent has a pinkish-purple with a darker eye flower color. In comparison to the new plant, the male parent has a much deeper golden-orange-colored flower.

The most similar daylily is 'When My Sweetheart Returns' (not patented) which has a smaller light yellow flower with broader rose eye around a greenish-yellow throat, and the flower is not as rounded or with the recurved tepal apex of 'Orange Smoothie'. 'Candy Peanuts' (not patented) has similar flowers in base color, but slightly more melon, and without the rose eye and green throat, with narrower outer tepals, less recurving to the apex, less wavy tepal margin and not as round in flower shape as 'Orange Smoothie'.

Other similar cultivars with dormant foliage and similar flower and plant size differ in that: 'Amerstone Amethyst Jewel' (not patented) the flower color is lilac amethyst with a yellow chartreuse green throat and the flower is not as rounded with the recurved tepal apex. 'Dreamboat Joseph' (not patented) but the flower color is pale yellow. 'Ink in the Snow' (not patented) the flower color is near white with a violet band around a near white throat. 'Isn't It Romantic' (not patented) the flowers have lavender rose colored tepals and a thinner wave or ruffle on the margin. 'Pink Tipped Pleasure' (not patented) has flowers that are butter cream-colored. 'Pinkle-purr' (not patented) has pink-colored flowers and without the heavy wavy tepal margins.

*Hemerocallis* 'Orange Smoothie' differs from all other daylilies known to the applicant, by the combination of the following traits:

1. Winter-hardy, compact habit with clean medium-green foliage that goes dormant in the winter;
2. Fragrant, single, rounded flowers about 10 cm across of orange-mango-colored base with light rose eye, pink midrib and light green throat;
3. Tepals with consistent and considerable wavy margins and recurved around apex giving more color from flower backside;
4. Plants produce concentrated scapes of about 60 cm tall with up to four branches and 32 flowers per scape;
5. Flowering begins about mid-July with excellent coverage and sending new scapes that flower through summer for about seven weeks;

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
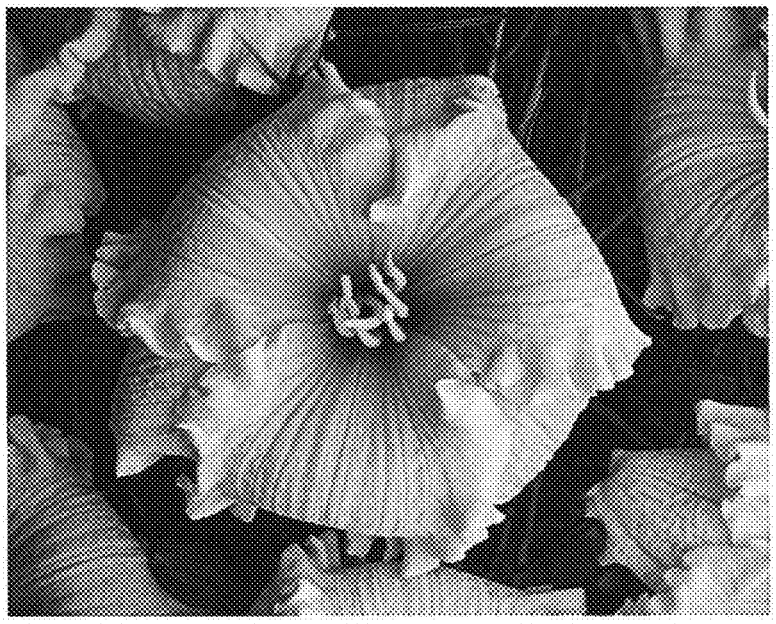
FIG. 1 shows a close-up of the flower.
Figure 2:
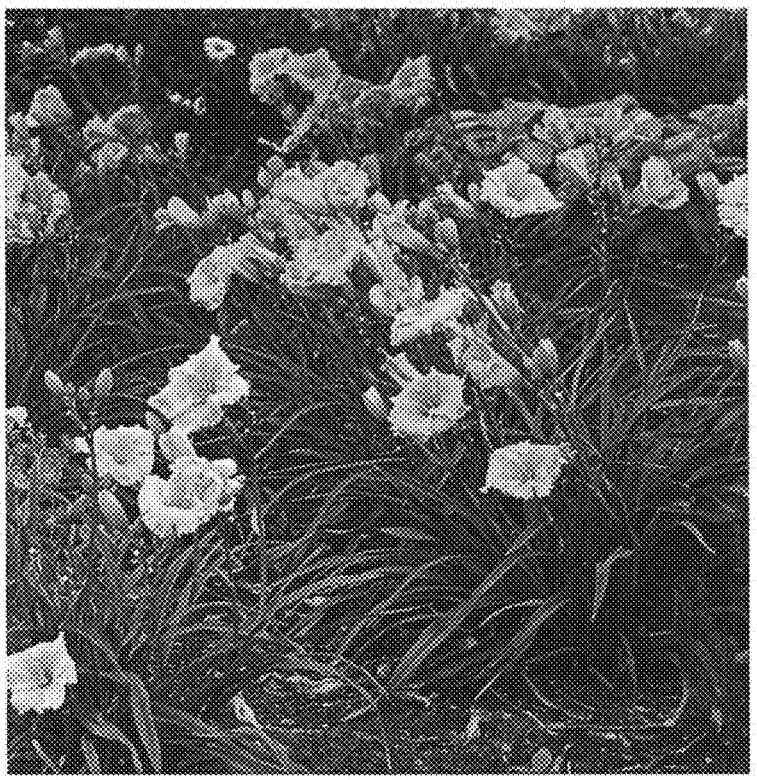
FIG. 2 shows a two-year-old plant in peak flower in a sunny landscape during mid-summer at a display garden in Zeeland, Mich.

The following descriptions and color references are based on the 2001 edition of The Royal Horticultural Society Colour Chart except where common dictionary terms are used. The new plant, *Hemerocallis* 'Orange Smoothie', has not been observed under all possible environments. The phenotype may vary slightly with different environmental conditions, such as temperature, light, fertility, moisture and maturity levels, but without any change in the genotype. The following observations and size descriptions are of a two-year-old plant in a sunny landscape at a display garden in Zeeland, Mich. with and supplemental water and fertilizer.

Botanical classification: *Hemerocallis* (L.) hybrid.

Parentage: Female (seed) parent is the proprietary unreleased hybrid *Hemerocallis* 95-104-2; male (pollen) parent is the proprietary unreleased hybrid *Hemerocallis* 96-20-5.

Propagation: Division of the rhizome.

Growth rate: Moderate to rapid.

Crop time: About 8 to 10 weeks to flower starting in spring in a 3.8 liter container from vernalized one-year-old plant.

Rooting habit: Fleshy, about 2.5 mm diameter; lightly branching.

Root color: Nearest RHS 159C depending on soil type.

Plant shape and habit: Winter-hardy herbaceous perennial with 14 to 18 basal shoots emerging from rhizomes producing a radially symmetrical mound of arching leaves.

Plant size: Foliage height about 44.0 cm tall from soil line to the top arch of the leaves and about 80.0 cm wide at the widest point.

Leaves: Entire, glabrous, slightly glaucous abaxial and adaxial, linear, sessile; apex narrowly acute, base sheathing; to about 58.0 cm long and 20.0 mm across, average about 56.0 cm long and about 15.0 mm across.

Cauline leaves: 1 to 2 per scape; reduced, average about 3.0 cm long and 8.0 mm across.

Leaf color: Young abaxial and adaxial nearest RHS 144A; mature adaxial nearest RHS 146B, mature abaxial nearest RHS 138A.

Veins: Parallel, slightly striate abaxial; color same as leaf abaxial and adaxial.

Flower description:

Flowers: Funnelform; single, with two sets of three tepals; 32 per scape, mostly distally arranged on about 4 branches; upward and outwardly facing; about 10.0 to 12.0 cm across and 7.0 cm deep; individually lasting for about one day; flowers remain effective from mid-July into late-August for approximately seven weeks in Zeeland, Mich.

Flower fragrance: Lightly sweet.

Buds one to two days prior to opening: Oblate ellipsoid with bluntly acute apex and basal one-fifth narrowed terete; about 7.0 cm long and about 28.0 mm in diameter at widest point with basal one-fifth narrowing to about 8.5 mm diameter.

Bud color one day from opening: Apical 5.0 mm between RHS 144A and RHS 144B, main central portion nearest RHS 22 B with faint overlay of nearest RHS 144B, narrowed base between RHS 146D and RHS 144B.

Tepals: 2 sets of 3; both sets recurved 270 degrees in distal one-fifth.

Inner tepals: Glabrous; rounded apex; consistently and considerably sinuate margins to about 1.0 cm deep and 1.0 cm across; base fused in proximal 2.0 cm; thickness at base about 2.0 mm; midrib raised about 2.0 mm on adaxial surface; about 4.5 cm across at widest point and about 9.5 cm long.

Outer tepals: Glabrous; rounded apex; slightly wavy outer margin of about 6.0 mm and central portion flat; fused in basal 2.0 cm; about 8.0 cm long and 6.5 cm across.

Inner tepal color adaxial starting distally: Outer orange band about 25 mm wide of between RHS 22C and RHS 22B; eye about 10.0 mm wide of nearest RHS 30D; thin yellow band of nearest RHS 13C melding into green throat reaching about 29.0 mm to base nearest RHS 143A; with a midrib of nearest RHS 29D.

Inner tepal color abaxial: Nearest RHS 22C.

Outer tepal color adaxial: 1.0 mm green apex nearest RHS 144A; between RHS 22 B and RHS 22C; melding into green base of nearest RHS 145A.

Outer tepal color abaxial, starting distally: 1.0 mm green apex nearest RHS 144A; middle portion between RHS 22B and RHS 23C, melding to base about 1.5 cm before narrow tube of nearest RHS N144D, and narrow tube nearest RHS N144D.

Pedicel: Approximately 10.0 mm long, 3.5 mm wide at base.

Pedicel color: Between RHS 139A and RHS 139C.

Peduncle: Usually one per division, erect to about 1.2 mm diameter at base, average 92.0 cm tall; extending above foliage.

Peduncle color: Between RHS 139A and RHS 139B.

Gynoecium: Single; tri-carpeled.

*Style*.—Single, about 8.0 cm long, 2.0 mm diameter, curled upward at distal one-third; color distally lighter than RHS 23D and proximally blend between RHS 145C and RHS 150C.

*Stigma*.—1.0 mm to 2.0 mm in diameter; color nearest RHS 150D.

*Ovary*.—Oval, about 6.0 mm long and 3.5 mm diameter at base with an acute apex; color nearest RHS 144A.

Androecium: Six.

*Filaments.*—Six; adnate to tepal; about 3.0 mm in diameter at base and 4.2 cm long from fusion point on tepal; curving slightly upward the last 2.0 cm; color distally nearest RHS 23B and proximally nearest RHS 145B.

*Anthers.*—Oblong; dorsifixed, longitudinal; about 6.0 mm long and 2.5 mm wide; color closest to RHS 200A.

*Pollen.*—Elliptical, less than 0.1 mm long; color nearest RHS 23A.

Fruit: Oblong ellipse; non-fleshy, dehiscent, many-seeded, tri-loculicidal capsule; ellipse; about 2.0 cm long and 1.2 cm in diameter; color while maturing nearest RHS 146C and at dehiscence nearest RHS 161B.

Seed: About 3 to 10 per capsule; nearly-round dried berry; about 4.0 mm diameter; color nearest RHS 202A.

Disease and pest resistance and tolerance: 'Orange Smoothie' has not shown resistance to diseases and pests beyond that common for daylilies, and given the northern testing regions the new plant has not been exposed to daylily rust, *Puccinia hemerocallidis*. The plant grows best and shows best coloration with plenty of moisture, adequate drainage and light shade during the hottest period of the day, but is able to tolerate some drought when mature and direct sun without leaf burn when provided sufficient water. Hardiness at least from USDA zone 3 through 9, and other disease resistance and tolerance is typical of that of other daylilies. The new plant is useful for landscaping en masse, as a single specimen or small groups.

The invention claimed is:

1. A new and distinct ornamental daylily plant named *Hemerocallis* 'Orange Smoothie' as herein described and illustrated.

* * * * *